(12) United States Patent
Eitan et al.

(10) Patent No.: US 12,214,162 B2
(45) Date of Patent: Feb. 4, 2025

(54) INFUSION PUMP WITH VALVE COMPENSATION

(71) Applicant: EITAN MEDICAL LTD., Netanya (IL)

(72) Inventors: Boaz Eitan, Hofit (IL); Amir Rasowsky, Yakir (IL); Gidi Pesach, Kfar Vitkin (IL); Ram Shtoltz, Givatayim (IL)

(73) Assignee: EITAN MEDICAL LTD., Netanya (IL)

( * ) Notice: Subject to any disclaimer, the term of this patent is extended or adjusted under 35 U.S.C. 154(b) by 835 days.

(21) Appl. No.: 17/433,388

(22) PCT Filed: Mar. 4, 2020

(86) PCT No.: PCT/IL2020/050246
§ 371 (c)(1),
(2) Date: Aug. 24, 2021

(87) PCT Pub. No.: WO2020/178824
PCT Pub. Date: Sep. 10, 2020

(65) Prior Publication Data
US 2022/0054745 A1    Feb. 24, 2022

Related U.S. Application Data

(60) Provisional application No. 62/813,897, filed on Mar. 5, 2019.

(51) Int. Cl.
*A61M 5/168* (2006.01)
*A61M 5/142* (2006.01)
*A61M 5/14* (2006.01)

(52) U.S. Cl.
CPC .... *A61M 5/16881* (2013.01); *A61M 5/14216* (2013.01); *A61M 5/16854* (2013.01);
(Continued)

(58) Field of Classification Search
None
See application file for complete search history.

(56) References Cited

U.S. PATENT DOCUMENTS

| 3,379,950 A | 4/1968 | Friedline |
| 4,236,880 A | 12/1980 | Archibald |

(Continued)

FOREIGN PATENT DOCUMENTS

| CN | 103727021 | 4/2014 |
| EP | 0182502 | 5/1986 |

(Continued)

OTHER PUBLICATIONS

Extended European Search Report for European Application No. 21194042.4, Dated Feb. 17, 2022., 7 pp.

(Continued)

*Primary Examiner* — Manuel A Mendez
(74) *Attorney, Agent, or Firm* — The Roy Gross Law Firm, LLC; Roy Gross (57) ABSTRACT

An infusion pump (100) includes a plunger (110) configured to squeeze a section of an infusion tube (150). A proximal valve (120), proximal to the plunger, ascends to allow infusion fluid intake from a reservoir to the infusion tube and descends to inhibit infusion fluid intake from the reservoir to the infusion tube. A distal valve (125), distal to the plunger, ascends to allow infusion fluid flow past the distal valve, and descends to inhibit infusion fluid flow past the distal valve. A controller (141) controls the plunger, proximal valve, and distal valve by initiating descending of the plunger concurrently with or prior to the ascending of the distal valve, such that the descending of the plunger compensates for suction produced by the ascending of the distal valve, thereby reducing backflow of fluid from the subject. Other applications are also described.

19 Claims, 3 Drawing Sheets

(52) U.S. Cl.
CPC ............... *A61M 2005/1406* (2013.01); *A61M 2205/332* (2013.01); *A61M 2205/3334* (2013.01)

(56) References Cited

U.S. PATENT DOCUMENTS

| | | | |
|---|---|---|---|
| 4,322,668 A | 3/1982 | Trussler et al. |
| 4,391,600 A | 7/1983 | Archibald |
| 4,650,469 A | 3/1987 | Berg et al. |
| 5,018,945 A | 5/1991 | D'Silva |
| 5,049,047 A | 9/1991 | Polaschegg et al. |
| 5,096,385 A | 3/1992 | Georgi et al. |
| 5,116,203 A | 5/1992 | Natwick et al. |
| 5,340,951 A | 8/1994 | Hungerbuhler et al. |
| 5,567,119 A | 10/1996 | Johnson et al. |
| 5,807,075 A | 9/1998 | Jacobsen et al. |
| 5,807,322 A | 9/1998 | Lindsey et al. |
| 5,843,035 A | 12/1998 | Bowman et al. |
| 6,312,227 B1 | 11/2001 | Davis |
| 6,494,864 B1 | 12/2002 | Kerwin et al. |
| 6,523,414 B1 | 2/2003 | Malmstrom et al. |
| 6,531,708 B1 | 3/2003 | Malmstrom et al. |
| 6,554,806 B2 | 4/2003 | Butterfield et al. |
| 6,659,976 B2 | 12/2003 | Beck et al. |
| 6,679,862 B2 | 1/2004 | Diaz et al. |
| 6,702,779 B2 | 3/2004 | Connelly et al. |
| 6,750,468 B2 | 6/2004 | Malmstrom et al. |
| 6,852,094 B2 | 2/2005 | Beck et al. |
| 6,889,556 B2 | 5/2005 | Steger |
| 6,907,788 B2 | 6/2005 | Malmstrom et al. |
| 6,908,452 B2 | 6/2005 | Diaz et al. |
| 6,979,311 B2 | 12/2005 | Miles et al. |
| 7,048,715 B2 | 5/2006 | Diaz et al. |
| 7,059,840 B2 | 6/2006 | Corwin et al. |
| 7,070,575 B2 | 7/2006 | Beck et al. |
| 7,092,796 B2 | 8/2006 | Vanderveen |
| 7,121,143 B2 | 10/2006 | Malmstrom et al. |
| 7,163,381 B1 | 1/2007 | Barak |
| 7,356,382 B2 | 4/2008 | Vanderveen |
| 7,384,408 B2 | 6/2008 | Barak |
| 7,497,842 B2 | 3/2009 | Diaz et al. |
| 7,695,448 B2 | 4/2010 | Cassidy et al. |
| 7,726,174 B2 | 6/2010 | Riley et al. |
| 7,758,551 B2 | 7/2010 | Wiesner et al. |
| 7,819,838 B2 | 10/2010 | Ziegler et al. |
| 7,875,004 B2 | 1/2011 | Yodfat et al. |
| 7,881,883 B2 | 2/2011 | Remde |
| 7,892,199 B2 | 2/2011 | Mhatre et al. |
| 7,896,197 B2 | 3/2011 | Furey et al. |
| 7,921,718 B2 | 4/2011 | Malmstrom et al. |
| 7,922,700 B2 | 4/2011 | Evans et al. |
| 7,967,773 B2 | 6/2011 | Amborn et al. |
| 7,981,082 B2 | 7/2011 | Wang et al. |
| 8,025,654 B2 | 9/2011 | Barak |
| 8,034,020 B2 | 10/2011 | Dewey |
| 8,048,022 B2 | 11/2011 | Moy et al. |
| 8,081,069 B2 | 12/2011 | Haueter et al. |
| 8,105,269 B2 | 1/2012 | Zhou |
| 8,142,400 B2 | 3/2012 | Rotem et al. |
| 8,152,780 B2 | 4/2012 | Evans et al. |
| 8,167,832 B2 | 5/2012 | Bowman et al. |
| 8,182,461 B2 | 5/2012 | Pope et al. |
| 8,225,639 B2 | 7/2012 | Riley et al. |
| 8,232,484 B2 | 7/2012 | Hauck |
| 8,286,505 B2 | 10/2012 | Wade |
| 8,287,495 B2 | 10/2012 | Michaud et al. |
| 8,298,184 B2 | 10/2012 | Diperna et al. |
| 8,328,786 B2 | 12/2012 | Strickler et al. |
| 8,343,111 B2 | 1/2013 | Beck et al. |
| 8,361,021 B2 | 1/2013 | Wang et al. |
| 8,378,837 B2 | 2/2013 | Wang et al. |
| 8,394,051 B2 | 3/2013 | Geipel |
| 8,419,676 B2 | 4/2013 | Evans et al. |
| 8,448,523 B2 | 5/2013 | Richter |
| 8,486,005 B2 | 7/2013 | Yodfat et al. |
| 8,486,020 B2 | 7/2013 | Hills et al. |
| 8,496,613 B2 | 7/2013 | Zhou |
| 8,539,672 B2 | 9/2013 | Eggers et al. |
| 8,567,235 B2 | 10/2013 | Bojan et al. |
| 8,641,671 B2 | 2/2014 | Michaud et al. |
| 8,657,778 B2 | 2/2014 | Ziegler et al. |
| 8,690,014 B2 | 4/2014 | Haueter et al. |
| 8,690,860 B2 | 4/2014 | Abal |
| 8,733,178 B2 | 5/2014 | Bivans et al. |
| 8,752,436 B2 | 6/2014 | Beck et al. |
| 8,758,323 B2 | 6/2014 | Michaud et al. |
| 8,771,227 B2 | 7/2014 | Connelly et al. |
| 8,795,225 B2 | 8/2014 | Lewis et al. |
| 8,808,230 B2 | 8/2014 | Rotstein |
| 8,821,432 B2 | 9/2014 | Unverdorben |
| 8,852,141 B2 | 10/2014 | Mhatre et al. |
| 8,859,972 B2 | 10/2014 | Cummings et al. |
| 8,876,787 B2 | 11/2014 | Beck et al. |
| 8,900,213 B2 | 12/2014 | Pope et al. |
| 8,926,561 B2 | 1/2015 | Verhoef et al. |
| 8,943,894 B2 | 2/2015 | Geipel |
| 8,945,064 B2 | 2/2015 | Gravesen et al. |
| 8,961,453 B2 | 2/2015 | Bowman et al. |
| 8,974,415 B2 | 3/2015 | Robert et al. |
| 8,986,253 B2 | 3/2015 | Diperna et al. |
| 9,004,886 B2 | 4/2015 | Beck et al. |
| 9,005,153 B2 | 4/2015 | Kopperschmidt et al. |
| 9,017,296 B2 | 4/2015 | Beck et al. |
| 9,033,923 B2 | 5/2015 | Hartman et al. |
| 9,101,712 B2 | 8/2015 | Denis et al. |
| 9,109,966 B2 | 8/2015 | Duits |
| 9,132,230 B2 | 9/2015 | Blomquist |
| 9,162,023 B2 | 10/2015 | Barnes et al. |
| 9,173,998 B2 | 11/2015 | Rosinko et al. |
| 9,211,377 B2 | 12/2015 | Diperna et al. |
| 9,227,008 B2 | 1/2016 | Magnenat et al. |
| 9,234,850 B2 | 1/2016 | Hammond et al. |
| 9,248,230 B2 | 2/2016 | Geipel et al. |
| 9,272,087 B2 | 3/2016 | Halbert et al. |
| 9,285,324 B2 | 3/2016 | Leuenberger Jockel |
| 9,308,323 B2 | 4/2016 | Adams |
| 9,375,531 B1 | 6/2016 | Lee et al. |
| 9,408,968 B2 | 8/2016 | Browne et al. |
| 9,415,158 B2 | 8/2016 | Miller et al. |
| 9,427,521 B2 | 8/2016 | Pope et al. |
| 9,468,713 B2 | 10/2016 | Hoenninger, III et al. |
| 9,474,854 B2 | 10/2016 | Mhatre et al. |
| 9,480,793 B2 | 11/2016 | Mhatre et al. |
| 9,480,794 B2 | 11/2016 | Keith et al. |
| 9,545,478 B2 | 1/2017 | Abal |
| 9,561,323 B2 | 2/2017 | Plahey et al. |
| 9,603,998 B2 | 3/2017 | Geipel et al. |
| 9,610,404 B2 | 4/2017 | Rotstein |
| 9,642,777 B2 | 5/2017 | Lewis et al. |
| 9,662,437 B2 | 5/2017 | Moosai |
| 9,675,756 B2 | 6/2017 | Kamen et al. |
| 9,677,555 B2 | 6/2017 | Kamen et al. |
| 9,682,192 B2 | 6/2017 | Marsh et al. |
| 9,683,562 B2 | 6/2017 | Davis et al. |
| 9,717,849 B2 | 8/2017 | Mhatre et al. |
| 9,757,517 B2 | 9/2017 | Eberhard |
| 9,770,552 B2 | 9/2017 | Hartman et al. |
| 9,775,947 B2 | 10/2017 | Keith et al. |
| 9,789,251 B2 | 10/2017 | Robert et al. |
| 9,839,744 B2 | 12/2017 | Muto et al. |
| 9,879,668 B2 | 1/2018 | Yavorsky et al. |
| 9,901,676 B2 | 2/2018 | Mijers et al. |
| 9,932,977 B2 | 4/2018 | Bresina et al. |
| 9,937,290 B2 | 4/2018 | Connelly et al. |
| 9,937,291 B2 | 4/2018 | Eberhard |
| 9,958,344 B2 | 5/2018 | Burkhard |
| 9,962,486 B2 | 5/2018 | Rosinko et al. |
| 9,987,424 B2 | 6/2018 | Kim |
| 9,995,642 B2 | 6/2018 | Shimoyama et al. |
| 10,004,847 B2 | 6/2018 | Wander et al. |
| 10,006,453 B2 | 6/2018 | Girard et al. |
| 10,022,494 B2 | 7/2018 | Shimizu |
| 10,022,495 B2 | 7/2018 | Halbert et al. |
| 10,022,496 B2 | 7/2018 | Geipel et al. |

(56) References Cited

U.S. PATENT DOCUMENTS

| | | |
|---|---|---|
| 10,046,112 B2 | 8/2018 | Oruklu et al. |
| 10,080,836 B2 | 9/2018 | Juretich et al. |
| 10,092,697 B2 | 10/2018 | Nessel et al. |
| 10,112,009 B2 | 10/2018 | Dudar et al. |
| 10,151,646 B2 | 12/2018 | Heo et al. |
| 10,539,453 B2 | 1/2020 | Hauck |
| 11,033,681 B2 | 6/2021 | Eitan et al. |
| 2003/0141468 A1 | 7/2003 | Malmstrom et al. |
| 2005/0107923 A1 | 5/2005 | Vanderveen |
| 2006/0173412 A1 | 8/2006 | Susi |
| 2006/0173421 A1 | 8/2006 | Weber et al. |
| 2006/0189926 A1 | 8/2006 | Hall et al. |
| 2006/0206054 A1 | 9/2006 | Shekalim |
| 2007/0123781 A1 | 5/2007 | Callahan et al. |
| 2007/0179435 A1 | 8/2007 | Braig et al. |
| 2008/0283296 A1 | 11/2008 | Zamora et al. |
| 2009/0240201 A1 | 9/2009 | Rotem et al. |
| 2009/0293588 A1 | 12/2009 | Riley et al. |
| 2010/0106082 A1* | 4/2010 | Zhou .............. A61M 5/14232 604/67 |
| 2010/0114001 A1 | 5/2010 | O'mahony |
| 2010/0212407 A1 | 8/2010 | Stringham et al. |
| 2010/0280446 A1 | 11/2010 | Kalpin |
| 2011/0087165 A1 | 4/2011 | Amborn et al. |
| 2011/0152772 A1 | 6/2011 | Rotem et al. |
| 2011/0190606 A1 | 8/2011 | Gable et al. |
| 2012/0205312 A1 | 8/2012 | Hogard |
| 2012/0238949 A1 | 9/2012 | Kalpin |
| 2012/0330574 A1 | 12/2012 | Ruiter et al. |
| 2013/0035659 A1 | 2/2013 | Hungerford et al. |
| 2013/0226129 A1 | 8/2013 | Unverdorben |
| 2013/0336814 A1 | 12/2013 | Kamen et al. |
| 2014/0066850 A1 | 3/2014 | Robert et al. |
| 2014/0119954 A1 | 5/2014 | Schweitzer et al. |
| 2014/0121639 A1 | 5/2014 | Lowery et al. |
| 2014/0214010 A1 | 7/2014 | Kuo et al. |
| 2014/0228755 A1 | 8/2014 | Darrah et al. |
| 2015/0005699 A1 | 1/2015 | Burbank et al. |
| 2015/0005732 A1 | 1/2015 | Halbert et al. |
| 2015/0238689 A1 | 8/2015 | Shimizu |
| 2015/0292500 A1 | 10/2015 | Girard et al. |
| 2015/0367120 A1 | 12/2015 | Kusters et al. |
| 2018/0140770 A1 | 5/2018 | Hetchler et al. |
| 2018/0200456 A1 | 7/2018 | Eitan et al. |
| 2018/0318505 A1 | 11/2018 | Eitan et al. |
| 2020/0282138 A1 | 9/2020 | Eitan et al. |
| 2021/0178062 A1 | 6/2021 | Eitan |
| 2021/0386931 A1 | 12/2021 | Eitan et al. |

FOREIGN PATENT DOCUMENTS

| | | | |
|---|---|---|---|
| EP | 1381843 | | 3/2009 |
| EP | 2040056 | | 9/2010 |
| EP | 2902052 | | 8/2015 |
| EP | 1381889 | | 3/2016 |
| EP | 2570826 | | 8/2016 |
| EP | 3705148 | A1 | 9/2020 |
| EP | 3834862 | | 6/2021 |
| FR | 2553151 | | 4/1985 |
| GB | 2150644 | | 7/1985 |
| WO | 02/068018 | | 9/2002 |
| WO | 2009/042061 | | 4/2009 |
| WO | 2009/047721 | | 4/2009 |
| WO | 2010/096449 | | 8/2010 |
| WO | 2012/126744 | | 9/2012 |
| WO | WO-2012126744 | A1 * | 9/2012 ........ A61M 5/14216 |
| WO | 2012/151077 | | 11/2012 |
| WO | 2013/184646 | | 12/2013 |
| WO | 2015/048093 | | 4/2015 |
| WO | 2017/184777 | | 10/2017 |
| WO | 2018/096534 | | 5/2018 |
| WO | 2019/155453 | | 8/2019 |
| WO | 2020/178824 | | 9/2020 |

OTHER PUBLICATIONS

An Office Action dated Sep. 30, 2019, which issued during the prosecution of U.S. Appl. No. 15/740,365.
European Search Report dated Jun. 21, 2019 which issued during the prosecution of European Application No. 16817348.2.
An International Search Report and a Written Opinion both dated Aug. 5, 2018, which issued during the prosecution of Applicant's PCT/IL2018/050409.
An Office Action dated Jun. 22, 2020, which issued during the prosecution of U.S. Appl. No. 15/740,365.
European Search Report dated Jun. 4, 2020, which issued during the prosecution of Applicant's European App No. 20160966.6.
An International Search Report and a Written Opinion both dated Jun. 9, 2020, which issued during the prosecution of Applicant's PCT/IL2020/050246.
European Search Report dated May 12, 2021 which issued during the prosecution of Applicant's European App No. 20212979.7.
An Office Action together with an English summary dated Jun. 23, 2020, which issued during the prosecution of Chinese Patent Application No. 201690050050.8.
European Search Report dated Apr. 22, 2021 which issued during the prosecution of Applicant's European App No. 20208122.0.
U.S. Appl. No. 62/813,897, filed Mar. 5, 2019.
European Search Report dated Oct. 8, 2021 which issued during the prosecution of Applicant's European App No. 18905766.4.
Notice of Allowance dated Aug. 4, 2021, which issued during the prosecution of U.S. Appl. No. 16/808,652.
An International Preliminary Report on Patentability dated May 28, 2019, which issued during the prosecution of Applicant's PCT/IL2017/051276.
An International Search Report and a Written Opinion both dated Jan. 19, 2018, which issued during the prosecution of Applicant's PCT/IL2017/051276.
An Office Action dated Aug. 12, 2020, which issued during the prosecution of U.S. Appl. No. 15/990,658.
An Office Action dated Mar. 26, 2020, which issued during the prosecution of U.S. Appl. No. 15/990,658.
An Advisory Action dated Jan. 13, 2021, which issued during the prosecution of U.S. Appl. No. 15/990,658.
Notice of Allowance dated Mar. 4, 2021, which issued during the prosecution of U.S. Appl. No. 15/990,658.
Notice of Allowance dated May 12, 2021, which issued during the prosecution of U.S. Appl. No. 15/990,658.

* cited by examiner

INFUSION PUMP WITH VALVE COMPENSATION

CROSS-REFERENCE TO RELATED APPLICATIONS

The present application is the US national stage application of PCT/IL2020/050246, filed Mar. 4, 2020, which published as PCT Publication WO 2020/178824 to Eitan et al., and which claims the priority of U.S. 62/813,897 to Eitan et al., filed Mar. 5, 2019 entitled, "Infusion pump with valve compensation," which is incorporated herein by reference.

FIELD OF THE INVENTION

The present invention relates generally to the field of medical devices for providing fluid to a patient. More specifically, the present invention relates to infusion pumps configured to inhibit bolus liquid flow and/or reverse flow by compensation for the descending and/or ascending of the pump's downstream valve.

BACKGROUND

Infusion pumps are configured to administer fluid to a patient via a conduit, such as an infusion tube or a cassette at high accuracy and often for a prolonged period of time. Infusion tubes are accommodated in the infusion pump in such manner that a plunger can squeeze the surface of the infusion tube, thereby causing delivery of the infusion fluid.

Infusion pumps administer fluids in ways that would be impractical and expensive/unreliable if performed manually by nursing staff. For example, an infusion pump assembly may repeatedly administer small quantities of an infusible fluid (e.g., 0.1 mL per hour).

SUMMARY OF THE INVENTION

A problem of infusion pumps, addressed by some applications of the present invention, is an unwanted suction of a patient's blood as a result of an ascending of the pump's downstream valve and/or an undesired bolus being provided to the patient as a result of a descending of the pump's downstream valve.

In accordance with some applications of the present invention, the herein disclosed infusion pump advantageously includes a controller configured to control the descending/ascending of the plunger along with the ascending/descending of the pump's distal valve, such that the flow caused by the ascending/descending of the pump's distal valve is compensated for by the plunger.

According to some embodiments, before or with opening the distal valve (also referred to herein as the downstream valve), the plunger is lowered, such that a volume of liquid, equal to the volume of blood that would otherwise be sucked into the infusion tube as a result of the ascending of the distal valve, is pumped towards the patient's open vein, thus counteracting/compensating for the unwanted backflow of blood.

Advantageously, such concurrent compensational movement of the plunger vis-à-vis the distal valve ensures that the flow rate of liquid into the patient is essentially devoid of spikes.

According to some embodiments, the valve may ascend and descend at a velocity that is correlated with a set flow rate. This may advantageously ensure that the volume pushed towards the patient by the descent of the downstream valve as well as the volume sucked by the ascent of the downstream valve do not momentarily alter the flow rate.

According to some embodiments, the upper position of the downstream/distal valve may be set such that while in its upper position the distal valve still squeezes the infusion tube in order to reduce boluses caused by the descending of the downstream valve. Advantageously, the distal valve still squeezing the infusion tube while in its upper position also minimizes power consumption, and thus cost of use. Additionally, the distal valve still squeezing the infusion tube while in its upper position ensures that the delivery of the infusion fluid is at an essentially constant volume regardless of a potential degradation of the infusion tube as well as inhibiting or at least reducing tube degradation.

There is therefore provided, in accordance with some applications of the present invention, an infusion pump including:
a plunger configured to squeeze a section of an infusion tube;
a proximal valve located proximally to said plunger, said proximal valve configured to:
  ascend and thereby allow infusion fluid intake from a reservoir to the infusion tube, and
  descend and thereby inhibit infusion fluid intake from the reservoir to the infusion tube;
a distal valve located distally to said plunger, said distal valve configured to:
  ascend and thereby allow infusion fluid flow past the distal valve, and
  descend and thereby inhibit infusion fluid flow past the distal valve; and
a controller configured to control said plunger, said proximal valve, and said distal valve and thereby, to control infusion fluid intake from the reservoir and infusion fluid delivery to a subject,
  wherein controlling delivery of infusion fluid to the subject includes initiating descending of said plunger concurrently with or prior to the ascending of said distal valve, such that the descending of said plunger compensates for suction produced by the ascending of said distal valve, thereby reducing backflow of fluid from the subject.

For some applications, a rate selected from the group consisting of: a rate of the ascending of the distal valve, and a rate of the descending of the distal valve, depends on a set flow rate of the infusion fluid.

For some applications, a rate of descending of the distal valve is determined based on a set flow rate and volume delivered as a result of the descending of the distal valve, wherein the volume delivered as a result of the descending of the distal valve is accounted for as a part of a total infusion fluid volume to be delivered.

For some applications, a motion of the plunger selected from the group consisting of: descending of the plunger, and ascending of the plunger, is continuous.

For some applications, a motion of the plunger selected from the group consisting of: descending of the plunger, and ascending of the plunger, is pulsatory.

For some applications, a motion selected from the group consisting of: the descending of the proximal valve, the ascending of the proximal valve, the descending of the distal valve, and the ascending of the distal valve, is continuous.

For some applications, a motion selected from the group consisting of: the descending of the proximal valve, the ascending of the proximal valve, the descending of the distal valve, and the ascending of the distal valve, is pulsatory.

For some applications, a rate selected from the group consisting of: a rate of ascending of the plunger, and a rate of descending of the plunger, depends on the set flow rate of the infusion fluid.

For some applications, a force sensor configured to measure the pressure in the part of the infusion tube extends between the proximal valve and the distal valve, and wherein the controller is configured to set a rate of the descending of the plunger based on the pressure measured by the force sensor.

For some applications, the distal valve is configured to ascend from a lower position to an upper position, wherein at both the upper position and the lower position, said distal valve is configured to squeeze a section of the infusion tube.

For some applications, the plunger is configured to descend from an upper position to a lower position, wherein at both the upper position and the lower position, said plunger is configured to squeeze a section of the infusion tube.

For some applications, a component of the infusion pump selected from the group consisting of: said plunger and said distal valve, is configured to contact an outer surface of the infusion tube from completion of intake to completion of delivery.

For some applications, the apparatus further includes a motor in communication with said controller, said motor configured to operate said plunger.

For some applications, said motor is further configured to operate at least one valve selected from the group consisting of: said proximal valve, and said distal valve.

For some applications, the apparatus further includes a second motor configured to operate at least one valve selected from the group consisting of: said proximal valve, and said distal valve.

For some applications, infusion tube is a DEHP-free PVC infusion tube, DEHP containing infusion tube, a polyethylene (PE) tube, a silicone tube, a thermoplastic elastomer (TPE) tube, a polypropylene (PP) tube, or a polyurethane tube.

There is further provided, in accordance with some applications of the present invention, an infusion pump including:
a plunger configured to squeeze a section of an infusion tube;
a proximal valve located proximally to said plunger, said proximal valve configured to ascend and to descend and thereby allowing and disabling, respectively, infusion fluid intake from a reservoir to the infusion tube;
a distal valve located distally to said plunger, said distal valve configured to:
ascend and thereby allow infusion fluid flow past the distal valve, and
descend and thereby inhibit infusion fluid flow past the distal valve; and
a controller configured to control said plunger, said proximal valve and said distal valve and thereby to control infusion fluid delivery to a subject and infusion fluid intake from an infusion source,
wherein the distal valve is configured to ascend from a lower position to a maximum upper position, wherein at both the maximum upper position and the lower position, said distal valve is configured to squeeze a section of an infusion tube.

For some applications, the ascending of the distal valve from the lower position to the upper position is an ascending from a complete tube occlusion position to a position where greater than 30%, but less than complete occlusion, of the area of the inner tube cross section of the infusion tube is squeezed.

For some applications, the ascending of the distal valve from the lower position to the upper position is performed at a predetermined rate.

For some applications, the ascending of the distal valve from a lower position to an upper position is an ascending from a position where less than 30% of the area of the inner tube cross section of the infusion tube is open to a position where 30%-98% of the area of the inner tube cross section is open.

For some applications, the ascending of the distal valve is performed concurrently with the descending of the plunger.

For some applications, a rate of the ascending of the distal valve depends on a set flow rate of the infusion fluid.

For some applications, a component of the infusion pump selected from the group consisting of: said plunger and said distal valve, is configured to contact an outer surface of the infusion tube from completion of intake to completion of delivery.

There is further provided, in accordance with some applications of the present invention, an infusion pump including:
a plunger configured to squeeze a section of an infusion tube;
a proximal valve located proximally to said plunger, said proximal valve configured to ascend and to descend and thereby allowing and disabling, respectively, infusion fluid intake from a reservoir to the infusion tube;
a distal valve located distally to said plunger, said distal valve configured to:
ascend and thereby allow infusion fluid flow past the distal valve, and
descend and thereby inhibit infusion fluid flow past the distal valve thereof;
a force sensor configured to measure the pressure in the part of the infusion tube extending between the proximal valve and the distal valve; and
a controller configured to control said plunger, said proximal valve and said distal valve and thereby to control infusion fluid delivery to a subject and infusion fluid intake from an infusion source,
wherein controlling delivery of infusion fluid to the subject comprises:
initiating descending of said plunger prior to or concurrently with an initial, partial ascending of said distal valve, wherein the initial partial ascending of the distal valve is independent of the set flow rate; and
initiating a continued ascending of the distal valve, wherein a rate of the continued ascending of the distal valve depends on a set flow rate set for the delivery of the infusion fluid and the pressure measured by the force sensor, such that an essentially constant delivery of infusion fluid is obtained.

For some applications, a component of the infusion pump selected from the group consisting of: said plunger and said distal valve, is configured to contact an outer surface of the infusion tube from completion of intake to completion of delivery.

For some applications, the descending of said plunger prior to an initial partial ascending of the distal valve is conducted at a predetermined rate.

For some applications, the descending of said plunger is conducted at a predetermined rate until a reduction of pressure in the infusion tube is detected upon ascending of the distal valve and opening of the infusion tube.

For some applications, the controller is configured to cause said plunger to descend concurrently with the continued ascending of the distal valve.

For some applications, a rate of the descending of the plunger is determined based on the pressure measured by the force sensor.

For some applications, a rate of the descending of the plunger is determined by the set flow rate for the delivery.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to the figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided an infusion pump comprising: a plunger configured to squeeze a section of an infusion tube; a proximal valve (also referred to herein as the "upstream valve") located proximally to the plunger; and a distal valve (also referred to herein as the "downstream valve") located distally to the plunger, wherein the distal valve is configured to ascend and thereby allow infusion fluid flow past the distal valve and to descend and thereby inhibit infusion fluid flow past the distal valve; and a controller configured to control the plunger, the proximal valve and the distal valve and thereby to control infusion fluid delivery to a subject and infusion fluid intake from an infusion source. According to some embodiments, the infusion pump further comprises a pressure sensor. According to some embodiments, the controller is configured to control movement of the plunger based on pressure measurements obtained from the pressure sensor.

According to some embodiments, the controller is configured to initiate an initial descending of the plunger prior to the ascending of the distal valve so as to create a positive pressure prior to the distal valve opening (while the proximal valve is closed) to compensate immediately for negative fluid flow that would otherwise result from ascending of the distal valve. According to some embodiments, the controller is configured to initiate a partial initial ascending of the distal valve. According to some embodiments, a partial initial ascending of the distal valve may form a discrete fluid path opening in accordance with a set flow rate requirement. Advantageously such partial initial ascending of the distal valve may better couple the negative and positive infusion fluid flows and thus reduce boluses. According to some embodiments, the controller is configured to initiate a partial descending of the plunger concurrently with the continued ascending of the distal valve (while the proximal valve is closed). According to some embodiments, this partial descending of the plunger depends on pressure in the section of an infusion tube measured by the pressure sensor. According to some embodiments, the above described descending of the plunger before or concurrently with the ascending of the distal valve may be referred to herein as a "compensatory" descending of the plunger that compensates for vacuum produced by the ascending of the distal valve, thereby reducing backflow of fluid from the subject. According to some embodiments, the descending of the plunger required for delivering the infusion fluid may be initiated once the distal valve reaches its upper position. As used herein, including in the claims, the term "upper position" of the distal valves refers to the maximum upper position of the distal valve in any given pump cycle, i.e., the upper limit of the distal valve stroke in any given pump cycle. According to some embodiments, the descending of the plunger required for delivering the infusion fluid may be initiated concurrently with the continued ascending of the distal valve to its upper position. According to some embodiments, this distal valve upper position may be dictated by pressure in the section of an infusion tube as measured by the pressure sensor.

According to some embodiments, the compensatory descending of the plunger may be performed separately from the descending of the plunger required for delivering the infusion fluid. According to some embodiments, the compensatory descending rate of the plunger may be same or different than the descending rate of the plunger required for delivering the infusion fluid. According to some embodiments, the compensatory descending of the plunger may be less than the descending of the plunger required for delivering the infusion fluid. According to some embodiments, the compensatory descending of the plunger may be coextensive with (an integral part of) the descending of the plunger required for delivering the infusion fluid.

Typically, the descending of the plunger being either (a) the compensatory descending of the plunger or (b) the descending of the plunger required for delivering the infusion fluid, depends on the state of the distal valve. While the distal valve is occluding the tube, the descending of the plunger is compensatory and acts to increase pressure in the isolated segment of the tube i.e., between the proximal and distal valves, thereby preparing a bolus that compensates for the suction that occurs when the distal valve is opened. For some set flow rates (e.g., less than 300 mL/h), the rate of the compensatory descending of the plunger is typically higher than the rate of the descending of the plunger required for delivering the infusion fluid.

The compensatory descending of the plunger is typically dependent on a predetermined volume of the bolus that compensates for the suction due to the ascending of the distal valve, which relates to parameters of the distal valve, e.g., the geometry of the distal valve, the stroke of the distal valve, and/or the size of the distal valve. Typically, the volume of the bolus prepared during the compensatory descending of the plunger is independent of the "set flow rate" of the infusion fluid (i.e., the flow rate which is set by an operator or programmer of the infusion pump). Contrary to the compensatory descending of the plunger, the descending of the plunger required for delivering the infusion fluid depends on the set flow rate of the infusion fluid.

According to some embodiments, the volume of the prepared bolus during the compensatory descending of the plunger may be calculated and accounted for as a part of the total delivered volume of infusion fluid. According to some embodiments, the compensatory descending of the plunger may be calculated according to pressure in the section of the infusion tube between the proximal and distal valves.

As used herein, the term "compensation" with regards to the plunger refers to a movement of the plunger which counteracts, nullifies, reverses, evens out or otherwise inhibits an undesired flow of infusion fluid to the patient's vein or reverse fluid/blood flow from the patient, caused by movement of the distal valve.

According to some embodiments, the distal valve is configured to ascend from a lower position, at which fluid delivery to the patient is essentially blocked, to an upper position, at which fluid delivery to the patient is facilitated. According to some embodiments, the ascending of the distal valve to the upper position may be minor such that the opening of the tube for delivery remains narrow (e.g. up to 30% area of the inner cross section of the infusion tube). Advantageously, at both the upper position and the lower position, the distal valve at least partially squeezes a section of the infusion tube, thereby reducing the volume of backflow caused by the ascending of the distal valve as well as enhancing the compensation for vacuum produced by the ascending of the distal valve and reducing power consumption. Advantageously, the smaller descending range of the valve reduces the positive flow bolus size.

According to some embodiments, descending of the plunger required for delivering the infusion fluid may be a descending of the plunger from an upper squeezing position to a lower squeezing position, wherein at both the upper squeezing position and the lower squeezing position, the plunger is squeezing a section of an infusion tube, such that an opposite side of an inner surface of the section does not contact the squeezed side, thus ensuring that the delivery of the infusion fluid is at an essentially constant volume regardless of a potential degradation of the infusion tube as well as inhibiting or at least reducing tube degradation.

As used herein, the term "infusion fluid" may refer to any fluid delivered to the patient such as, but not limited to, insulin, nutrients, saline solution, antibiotics, analgesics, anesthetics, hormones, vasoactive drugs, and chelation drugs, and any other therapeutic fluids or combination of fluids.

As used herein, the term "upper squeezing position" with regards to the plunger, refers to a position of a plunger at which an infusion tube is mildly squeezed (i.e. lower than a position at which the tube is not squeezed), without having the opposite sides of an inner surface of the squeezed section contacting one another. According to some embodiments, the delivery phase of the infusion pump is initiated at the "upper squeezing position" or at "after compensation" position. According to some embodiments, the upper squeezing position is higher (less squeezing of the tube) than the position of the plunger when descended to compensate for the backflow caused by the ascending of the distal valve.

As used herein, the term "lower squeezing position" with regards to the plunger, refers to a position of the plunger at which an infusion tube is squeezed to a larger extent as compared to the upper squeezing position, yet still without having the opposite sides of an inner surface of the squeezed section contacting one another.

As used herein, the term "degradation" may refer to the tube losing its springiness, becoming deformed, bottoming out, or otherwise changing its shape or consistency in a manner affecting the drug delivery accuracy. According to some embodiments, the infusion tube may be a DEHP-free PVC infusion tube, a DEHP containing infusion tube, a polyethylene (PE) tube, a silicone tube, a polyurethane tube or the like. Each possibility is a separate embodiment.

According to some embodiments, the velocity of the ascending and descending of the distal valve and/or of the plunger depends on the set flow rate of the infusion fluid. According to some embodiments, the ascending and/or descending of the plunger may be continuous, i.e. at a constant rate. According to some embodiments, the ascending and/or descending of the plunger may be pulsatory, i.e. in small steps. According to some embodiments, the ascending and/or descending of the distal valve may be continuous, i.e. at a constant rate. According to some embodiments, the ascending and/or descending of the distal valve may be pulsatory, i.e. in small steps. That is, at high set flow rates, the velocity of the ascending and descending of the distal valve and/or of the plunger may likewise be high, and at low set flow rates, the velocity of the ascending and descending of the distal valve and/or of the plunger may likewise be low. According to some embodiments, the controller may be configured to automatically adjust the velocity of the ascending and descending of the distal valve and/or of the plunger according to the set flow rate. This ascending/descending sequence and control of movement allow continued fluid delivery flow. For example, the controller may adjust the rate of the descending of the distal valve based on the set flow rate in order to avoid a bolus delivery upon descending of the distal valve, i.e., the rate of the descending of the distal valve is controlled by the controller such that as the distal valve descends the distal valve pushes infusion fluid to the subject at the set flow rate. Thus, for higher flow rates, i.e., faster descending of the plunger, a faster descending of the distal valve may be set, and for lower flow rates, i.e., slower descending of the plunger, a slower descending of the distal valve may be set. The extra volume of fluid pushed to the subject during the descending of the distal valve may be calculated and accounted for as part of the volume of infusion fluid delivered per pump cycle.

Typically, the "upper position" of the distal valve refers to a position of the distal valve at which an infusion tube is squeezed (i.e. lower than a position at which the tube is not squeezed), without having the opposite sides of an inner surface of the squeezed section contacting one another. That is, at the upper position the distal valve engages the infusion tube.

As used herein, the term "lower position" with reference to the distal valve refers to a position of the distal valve at which the infusion tube is squeezed to such extent that delivery of infusion fluid to the patient is essentially avoided.

According to some embodiments, the inner tube cross section of the infusion tube when the distal valve is in its upper position is 30%-98% (e.g., a preset value, e.g., 50%) of the area of the inner tube cross section of the infusion tube, when non-squeezed. Various upper positions for the distal valve may be used, affecting the percentage of the squeezed area, for different set flow rates. For example, while in its upper position the distal valve still squeezes the infusion tube in order to reduce the bolus that is caused by the descending of the distal valve. Nevertheless, while in its upper position the distal valve should be open enough so as not to inhibit delivery of the infusion fluid during the descending of the plunger.

According to some embodiments, for a typical tube of 3 mm inner diameter and a wall thickness of 0.5 mm, a typical upper position, of the distal valve is about 0.3 mm to 2.8 mm, lower than the diameter of a non-squeezed tube. Each possibility is a separate embodiment.

According to some embodiments, the infusion pump is configured to maintain an essentially constant flow rate during the entire delivery of an infusion fluid. As a non-limiting example, the infusion pump is configured to maintain a delivery of an infusion fluid at a set flow rate of 1±0.05 mL/hour for at least 20, at least 36 or at least 96 hours.

According to some embodiments, the pump further includes a motor in communication with the controller, the motor configured to operate the plunger. According to some embodiments, the motor may further be configured to operate the proximal valve, the distal valve or both. Alternatively, the pump may include one or two additional motors configured to operate the proximal valve, the distal valve or both. According to some embodiments, the controller may control the operation of the motor, thereby determining the exact position of the plunger and/or the distal valve. According to some embodiments, the controller may control the operation of the motor, by determining a velocity/rate of the ascending/descending of the plunger, the proximal valve and/or the distal valve. According to some embodiments, the controller may control the operation of the motor, by determining the increments of the ascending/descending of the plunger, the proximal valve and/or the distal valve. According to some embodiments, the controller may control the operation of the motor, by determining the value of the ascending/descending of the plunger, the proximal valve and/or the distal valve.

According to some embodiments, the controller may further be configured to determine a "wait" period, during which the plunger remains at the upper squeezing position, thereby ensuring full engagement of the infusion tube with the plunger, prior to the closing of the infusion pump's upstream valve. This advantageously increases the accuracy of infusion fluid delivery in that the volume delivered remains constant even if the infusion tube has undergone degradation.

Furthermore, due to the infusion tube fully engaging the plunger, a persistent ascending of the infusion tube after opening of the upstream valve is essentially inhibited. The length of the wait depends on the flow continuity requirements and the set flow rate. For low set flow rates (0.1-1 mL/hr) and flow continuity of bolus every 20 sec, the wait can last up to 18 sec. For higher set flow rates, the wait time can be shorter (e.g. about 10 sec) and for very high flow rates (999 mL/hr) it may last less than 1 second. The long wait is particularly advantageous for low set flow rates where the tube squeeze duty cycle is very long. The long wait times are essentially a no movement of plunger and valves in the specific position while for high set flow rates the "wait" equals pump's check-in time—the time the pump goes through the encoders that leave the plunger in the upper position while the proximal valve is open.

According to some embodiments, there is provided a method of operation of an infusion pump, the method comprising utilizing the infusion pump, as essentially described herein.

Figure 1:
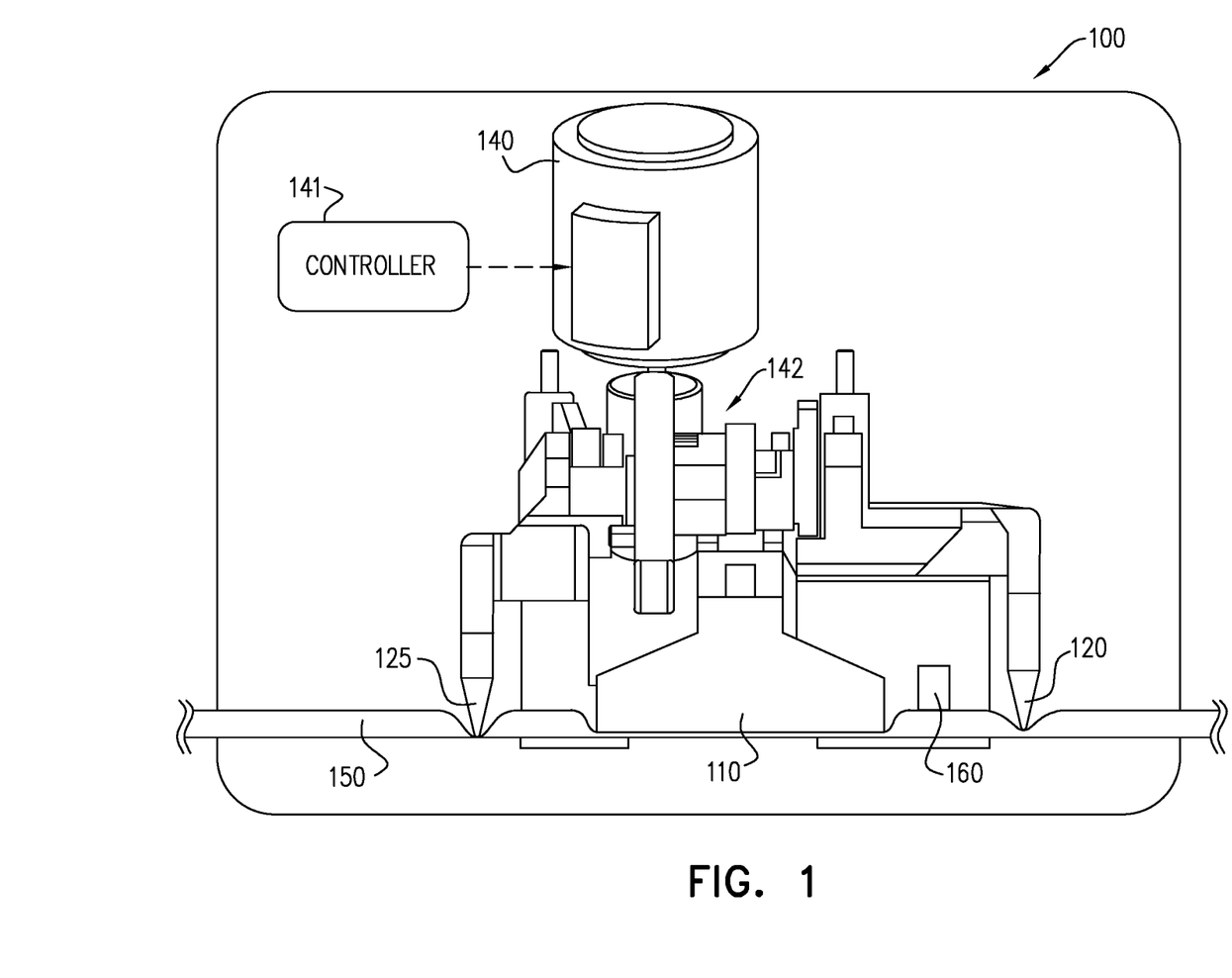
FIG. 1 schematically illustrates an infusion pump, according to some embodiments.

Reference is now made to FIG. 1 which schematically illustrates an infusion pump 100 with a plunger 110, a proximal/upstream valve 120, also referred to herein as an inlet valve, positioned proximally/upstream to plunger 110 and configured to allow flow of infusion fluid from a reservoir (not shown) to an infusion tube 150 and a distal/downstream valve 125, also referred to herein as an outlet valve, positioned distally/downstream to plunger 110 and configured to allow flow of infusion fluid from infusion tube 150 to a patient (not shown). The positioning of plunger 110, proximal valve 120 and distal valve 125 are carried out by motor 140 and associated cam shaft 142, although other embodiments, according to which positioning of plunger 110, proximal valve 120 and distal valve 125 is executed by separate motors, are also possible and within the scope of this disclosure. Motor 140 is typically controlled by a controller 141. Infusion pump 100 further includes a force sensor 160 configured to measure the pressure in the part of infusion tube 150 extending between proximal valve 120 and distal valve 125. The figure illustrates the pump at a state when proximal valve 120 is at a tube releasing position, distal valve 125 is at a tube occluding position and plunger 110 is at a tube squeezing position.

Figure 2A:
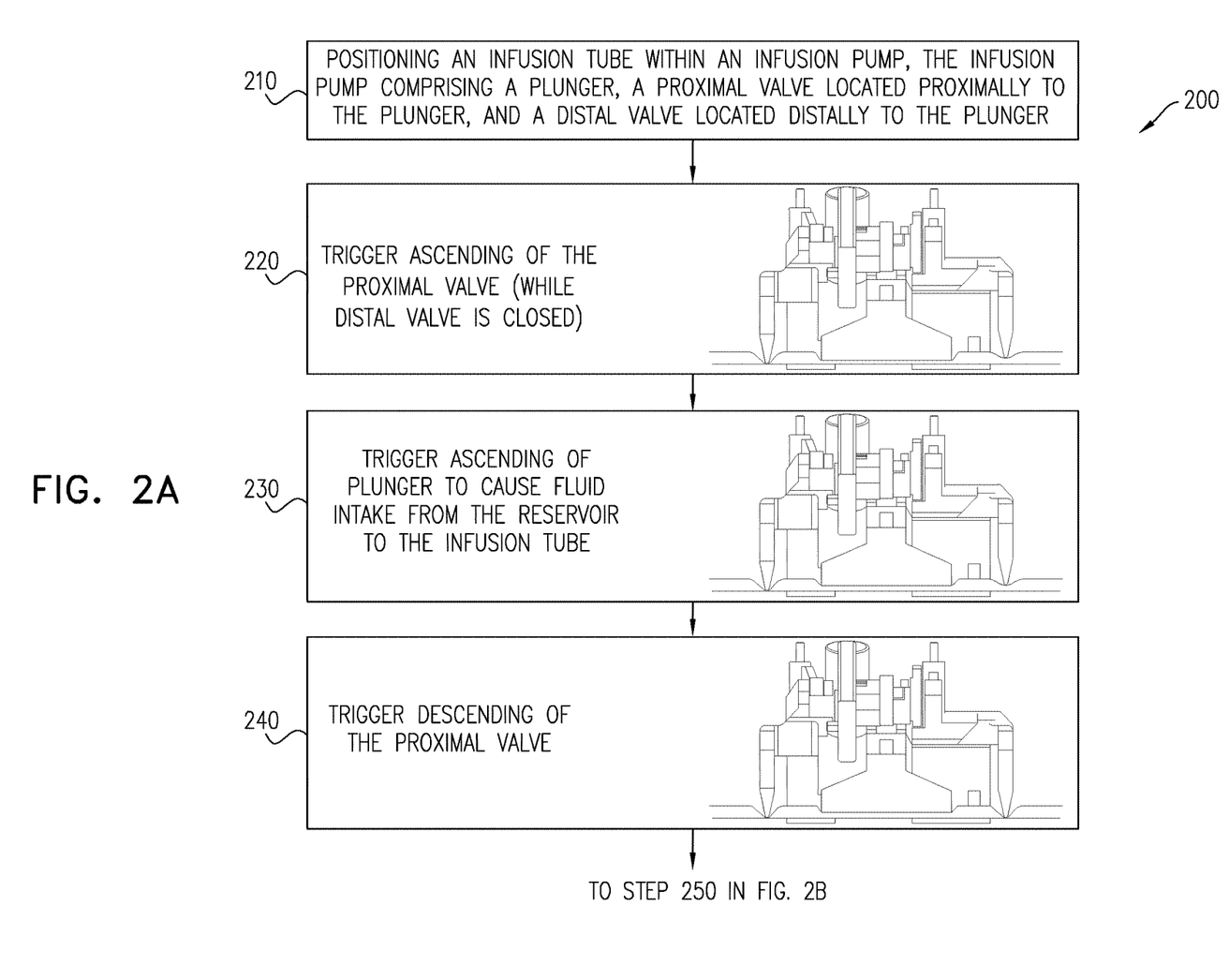
FIGS. 2A-B are, combined, an illustrative flowchart for operating an infusion pump, according to some embodiments.
Figure 2B:
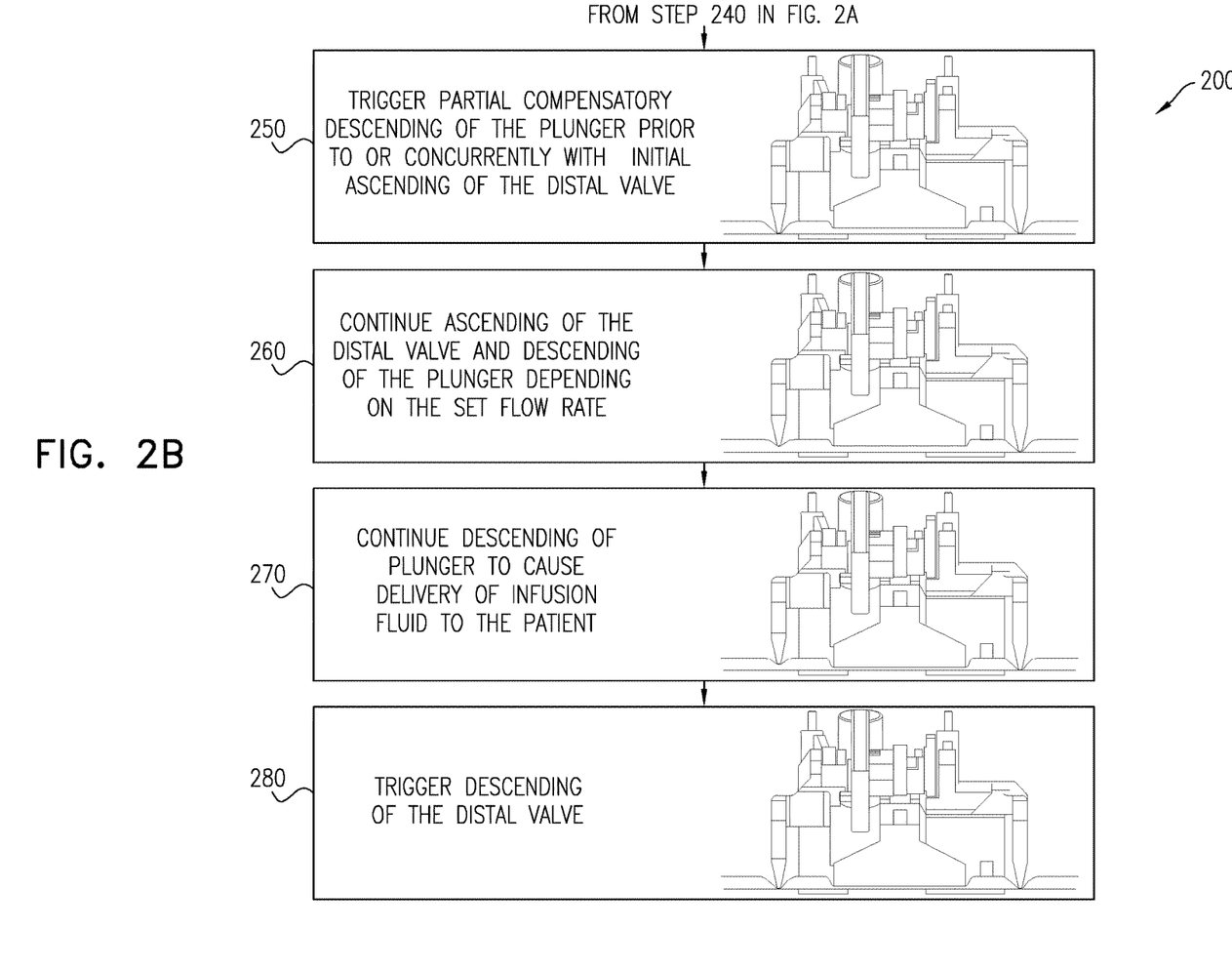

Reference is now made to FIGS. 2A-B which are, combined, an illustrative flowchart 200 for operating an infusion pump, according to some embodiments.

In step 210 an infusion tube is positioned within an infusion pump, the infusion pump comprising a plunger, a proximal valve located proximally to the plunger, and a distal valve located distally to the plunger.

Steps 220 to 240 are steps associated with intake of infusion fluid from a reservoir (also referred to herein as infusion source).

In step 220 an opening of the proximal valve is initiated (while the distal valve is closed), thereby establishing a fluid flow connection between the reservoir and the infusion tube.

In step 230 the plunger is caused to ascend, thereby causing intake of fluid from a reservoir. The ascending of the plunger, causing intake of the infusion fluid from the reservoir, is only initiated once the distal valve has reached its lower position at which the fluid flow connection between the infusion tube and the patient's vein has been closed.

In step 240 descending of the proximal valve is initiated to occlude the fluid line to terminate the fluid intake. The occlusion of the fluid line by proximal valve is completed before the distal valve starts ascending, thereby providing a phase where both valves are closed, during which the compensation step is carried out.

Steps 250 to 280 are steps associated with delivery of the infusion fluid to a patient.

In step 250 a partial, compensatory descending of the plunger is initiated prior to or concurrently with an initial ascending of the distal valve, thereby generating a positive pressure in the tube. Typically, up to 30% of the area of the inner tube cross section of the infusion tube is opened during the initial ascending motion of the distal valve. The compensatory descending of the plunger is configured to ensure that backflow of blood from the patient's vein into the infusion tube, as a result of the ascending of the distal valve, is reduced or inhibited. It is understood that the method alternatively may include two separate steps; a first step (e.g.

step 250*a*) of partial compensatory descending of the plunger prior to the initial ascending of the distal valve and a second step (e.g. step 250*b*) of additional compensatory descending of the plunger concurrently with the ascending of the distal valve. During this step (250 or 250*b*), the pressure in the infusion tube between the valves is measured by the force sensor. If a decrease in pressure is observed, indicating that the distal valve has opened and downstream flow of infusion fluid is facilitated, the plunger transitions to descending at a rate corresponding to the set flow rate of the infusion fluid. It is noted that in the illustrative figure of step 250 the plunger and the distal valve appear to be in the same position as they are in the illustrative figure of step 240. The partial compensatory descending of the plunger is small and therefore not noticeably shown in the figure. Additionally, the distal valve is shown closed, since the partial compensatory descending of the plunger may occur prior to the initial ascending of the distal valve.

In step 260 the ascending of the distal valve and the descending of the plunger is continued. According to some embodiments, the rate of the ascending of the distal valve increases with the set flow rate, e.g., for higher set flow rates the distal valve ascends at a higher rate.

Optionally, in step 270 the plunger is further lowered thereby causing the infusion fluid to be delivered to the patient. Alternatively, the continuous ascending of the distal valve in step 260 may be very slow and prolonged, such that the delivery of the infusion fluid becomes an integral part of step 260.

In step 280, upon the plunger having completed the squeezing of the infusion tube, a descending of the distal valve is initiated to occlude the infusion line. The volume delivered due to descending of the distal valve may be determined and taken into account as part of the total volume of infusion fluid delivered, as described hereinabove. The rate of the descending of the distal valve may be adjusted to match the set flow rate of delivery.

It is understood that upon completion of infusion fluid delivery, additional intake/delivery cycles may be performed by repeating steps 220 through 280.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, steps, operations, elements, or components, but do not preclude or rule out the presence or addition of one or more other features, steps, operations, elements, components, or groups thereof.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system (e.g., controller 141), or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general-purpose computer selectively activated or reconfigured by a computer program stored in the computer. Such a computer program may be stored in a computer readable storage medium, such as, but not limited to, any type of Non-volatile memory (NVM), or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of some of the inventions as described herein.

Embodiments of the invention may be described in the general context of computer-executable instructions, such as program modules, being executed by a computer. Generally, program modules include routines, programs, objects, components, data structures, and so forth, which perform particular tasks or implement particular abstract data types. Embodiments of the invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. An infusion pump comprising:
   a plunger configured to squeeze a section of an infusion tube;
   a proximal valve located proximally to said plunger, said proximal valve configured to:
      ascend and thereby allow infusion fluid intake from a reservoir to the infusion tube, and
      descend and thereby inhibit infusion fluid intake from the reservoir to the infusion tube;
   a distal valve located distally to said plunger, said distal valve configured to:
      ascend and thereby allow infusion fluid flow past the distal valve, and
      descend and thereby inhibit infusion fluid flow past the distal valve; and
   a controller configured to control said plunger, said proximal valve, and said distal valve and thereby, to control infusion fluid intake from the reservoir and infusion fluid delivery to a subject,
   wherein controlling delivery of infusion fluid to the subject comprises initiating descending of said plunger prior to the ascending of said distal valve, such that the descending of said plunger compensates for suction produced by the ascending of said distal valve, thereby reducing backflow of fluid from the subject.

2. The infusion pump of claim 1, wherein a rate selected from the group consisting of: a rate of the ascending of the distal valve, and a rate of the descending of the distal valve, depends on a set flow rate of the infusion fluid.

3. The infusion pump of claim 1, wherein a rate of descending of the distal valve is determined based on a set flow rate and volume delivered as a result of the descending of the distal valve, wherein the volume delivered as a result of the descending of the distal valve is accounted for as a part of a total infusion fluid volume to be delivered.

4. The infusion pump of claim 1, wherein a motion selected from the group consisting of: the descending of the proximal valve, the ascending of the proximal valve, the descending of the distal valve, and the ascending of the distal valve, is continuous.

5. The infusion pump of claim 1, wherein a motion selected from the group consisting of: the descending of the proximal valve, the ascending of the proximal valve, the descending of the distal valve, and the ascending of the distal valve, is pulsatory.

6. The infusion pump of claim 1, further comprising a force sensor configured to measure the pressure in the part of the infusion tube extending between the proximal valve and the distal valve, and wherein the controller is configured to set a rate of the descending of the plunger based on the pressure measured by the force sensor.

7. The infusion pump of claim 1, wherein the distal valve is configured to ascend from a lower position to an upper position, wherein at both the upper position and the lower position, said distal valve is configured to squeeze a section of the infusion tube.

8. The infusion pump of claim 1, wherein the plunger is configured to descend from an upper position to a lower position, wherein at both the upper position and the lower position, said plunger is configured to squeeze a section of the infusion tube.

9. The infusion pump of claim 1, wherein a component of the infusion pump selected from the group consisting of: said plunger and said distal valve, is configured to contact an outer surface of the infusion tube from completion of intake to completion of delivery.

10. The infusion pump of claim 1, further comprising a motor in communication with said controller, said motor configured to operate said plunger.

11. The infusion pump of claim 10, wherein said motor is further configured to operate at least one valve selected from the group consisting of: said proximal valve, and said distal valve.

12. The infusion pump of claim 10, further comprising a second motor configured to operate at least one valve selected from the group consisting of: said proximal valve, and said distal valve.

13. The infusion pump of claim 1, wherein controlling delivery of infusion fluid to the subject further comprises, subsequently to the ascending of said distal valve, controlling said plunger to deliver infusion fluid to the subject by descending further.

14. An infusion pump comprising:
a plunger configured to squeeze a section of an infusion tube;
a proximal valve located proximally to said plunger, said proximal valve configured to ascend and to descend and thereby allowing and disabling, respectively, infusion fluid intake from a reservoir to the infusion tube;
a distal valve located distally to said plunger, said distal valve configured to:
ascend and thereby allow infusion fluid flow past the distal valve, and
descend and thereby inhibit infusion fluid flow past the distal valve; and
a controller configured to control said plunger, said proximal valve and said distal valve and thereby to control infusion fluid delivery to a subject and infusion fluid intake from an infusion source,
wherein the distal valve is configured to ascend from a lower position to a maximum upper position, wherein at both the maximum upper position and the lower position, said distal valve is configured to squeeze a section of an infusion tube.

15. The infusion pump of claim 14, wherein the ascending of the distal valve from the lower position to the upper position is an ascending from a complete tube occlusion position to a position where greater than 30%, but less than complete occlusion, of the area of the inner tube cross section of the infusion tube is squeezed.

16. The infusion pump of claim 15, wherein the ascending of the distal valve from the lower position to the upper position is performed at a predetermined rate.

17. The infusion pump of claim 14, wherein the ascending of the distal valve from a lower position to an upper position is an ascending from a position where less than 30% of the area of the inner tube cross section of the infusion tube is open to a position where 30%-98% of the area of the inner tube cross section is open.

18. The infusion pump of claim 14, wherein initiating the ascending of the distal valve is performed concurrently with or following initiation of the descending of the plunger.

19. The infusion pump of claim 14, wherein a rate of the ascending of the distal valve depends on a set flow rate of the infusion fluid.

* * * * *